US007933648B2

(12) United States Patent
Tanrisever

(10) Patent No.: US 7,933,648 B2
(45) Date of Patent: Apr. 26, 2011

(54) HIGH VOLTAGE TRANSCUTANEOUS ELECTRICAL STIMULATION DEVICE AND METHOD

(75) Inventor: Naim Erturk Tanrisever, Bostanci (TR)

(73) Assignee: Naim Erturk Tanrisever, Bostanci (TR)

( * ) Notice: Subject to any disclaimer, the term of this patent is extended or adjusted under 35 U.S.C. 154(b) by 182 days.

(21) Appl. No.: 11/491,201

(22) Filed: Jul. 21, 2006

(65) Prior Publication Data
US 2007/0055337 A1 Mar. 8, 2007

Related U.S. Application Data

(60) Provisional application No. 60/701,263, filed on Jul. 21, 2005.

(51) Int. Cl.
A61N 1/04 (2006.01)

(52) U.S. Cl. .................. 607/2; 607/76; 607/115

(58) Field of Classification Search .................. 607/1, 2, 607/76, 115, 116
See application file for complete search history.

(56) References Cited

U.S. PATENT DOCUMENTS

| 1,951,731 | A | * | 3/1934 | Kassner | 607/156 |
|---|---|---|---|---|---|
| 2,460,707 | A | * | 2/1949 | Moray | 600/2 |
| 3,399,667 | A | * | 9/1968 | Nishimoteto et al. | 600/302 |
| 3,666,651 | A | * | 5/1972 | Makabe | 204/420 |
| 4,233,986 | A | | 11/1980 | Tannenbaum | |
| 4,305,402 | A | | 12/1981 | Katims | |
| 4,357,497 | A | | 11/1982 | Hochmair et al. | |
| 4,503,863 | A | | 3/1985 | Katims | |
| 4,667,677 | A | * | 5/1987 | Di Mino | 607/71 |
| 4,919,148 | A | | 4/1990 | Muccio | |
| 5,186,171 | A | | 2/1993 | Kuhry | |
| 5,205,297 | A | | 4/1993 | Montecalvo et al. | |
| 5,218,973 | A | | 6/1993 | Weaver et al. | |
| 5,260,313 | A | | 11/1993 | Frome | |
| 5,324,317 | A | | 6/1994 | Reiss | |
| 5,350,414 | A | | 9/1994 | Kolen | |
| 5,374,283 | A | | 12/1994 | Flick | |
| 5,397,338 | A | | 3/1995 | Grey et al. | |
| 5,573,552 | A | | 11/1996 | Hansjurgens | |
| 5,643,331 | A | | 7/1997 | Katz | |
| 5,723,001 | A | | 3/1998 | Pilla et al. | |
| 5,728,141 | A | | 3/1998 | Calbet Benach et al. | |
| 5,823,989 | A | | 10/1998 | Ostrow | |

(Continued)

OTHER PUBLICATIONS

Necmi Kurt, et al., "Locally Used High Voltage Stimulation Therapy in Burn Patients," *Cagadas Cerrahi Dergisi*, 2000, 178-182, vol. 14.

(Continued)

Primary Examiner — Scott M Getzow
Assistant Examiner — Joseph M Dietrich
(74) Attorney, Agent, or Firm — RatnerPrestia

(57) ABSTRACT

The invention comprises a system for treating a medical disorder using transcutaneous electrical stimulation. The system includes an apparatus that supplies voltage to one or more glass electrodes that is shaped to treat a particular tissue or disorder and that is applied to an affected area of the patient's body. Voltage is applied in a range of about 500-2000 volts and a constant frequency in a range of about 10-100 kHz. The electrode may also be used to sterilize the surface of a tissue through the production of ozone. The system may be used to treat a variety of medical disorders including edema and dermatological, neurological, intestinal, vascular, and orthopedic disorders. In addition, the system may be used to improve drug delivery to specific sites by locally increasing blood circulation.

38 Claims, 14 Drawing Sheets

U.S. PATENT DOCUMENTS

| | | |
|---|---|---|
| 5,871,534 A | 2/1999 | Messick et al. |
| 6,101,418 A | 8/2000 | Benach |
| 6,161,044 A | 12/2000 | Silverstone |
| 6,351,674 B2 | 2/2002 | Silverstone |
| 6,429,217 B1 | 8/2002 | Puskas |
| 6,697,670 B2 | 2/2004 | Chomenky et al. |
| 6,763,264 B2 | 7/2004 | Hofmann |
| 6,792,315 B2 | 9/2004 | Carter et al. |
| 6,907,294 B2 | 6/2005 | Andino et al. |
| 6,916,294 B2 | 7/2005 | Ayad |
| 2003/0195590 A1* | 10/2003 | Carter et al. .......... 607/69 |

OTHER PUBLICATIONS

Erturk Tanrisever, "Korona Tedavi Cihazi", Blyomut 96, 1996, pp. 193-198, Turkey.

* cited by examiner

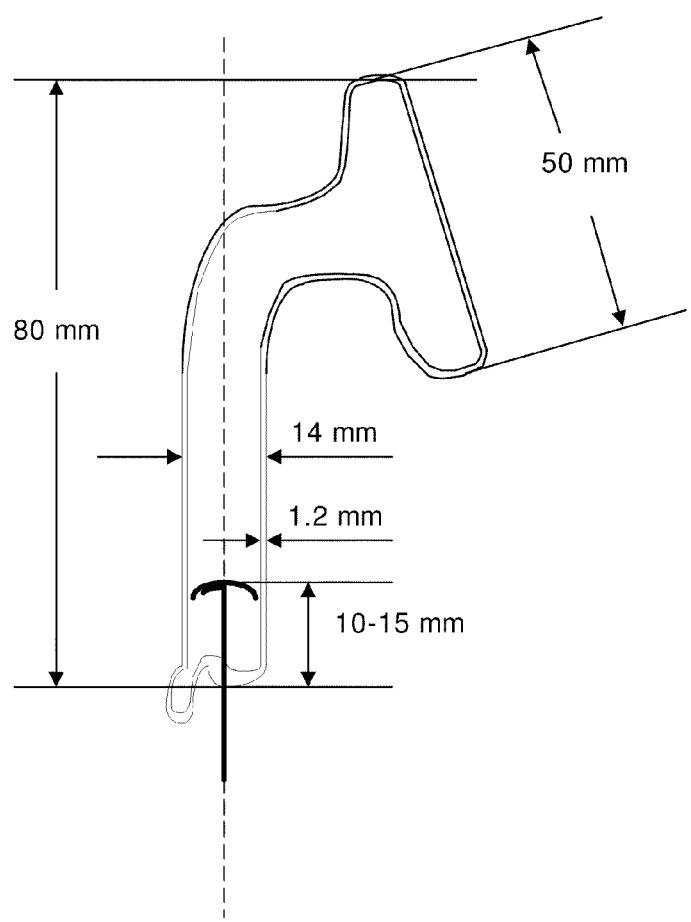
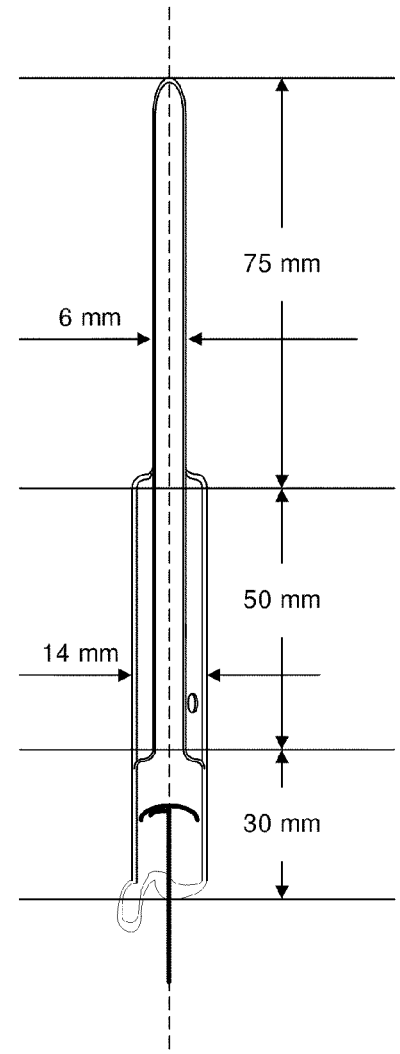
FIG. 7  FIG. 8

Circuit BI1-120V $R1 = 470K$
$R2 = 220K$    $C1 = 150nF$
$R_3 = 15K$    $C_2 = 47nF$
$R_4 = 220$    $C_3 = 10nF$
$R_5nL = 10$    $C_4 = 4.7\mu F$
$R_{13} = 1K$    $C_5 = 47\mu F$
$R_{17} = 6.2K$    $C_6 = 20\mu F / 400V$    $D_1 = Z15$
$R_{28} = 1/1w$    $C_7 = 15nF$    $D_2 = 50V$
$P1 = 470K$    $C_8 = 15nF$    $D_3 = 1N4005$
$P_2 = 10K$    $C_{22} = 10\mu F$    $L_2 = 0.82mH / 0.5A / 5ohm$
$P_3 = 100K$    $C_{24} = 150nF$ $V_{top} = \sqrt{2} * 120 = 170$    $TY_1 = Triac$
$V_+ = 2*V_{top} = 2*170 = 340V$    $= BT138 / 500V / 12A$
     $= MAC210 / 600 ?V / 10A$

HIGH VOLTAGE TRANSCUTANEOUS ELECTRICAL STIMULATION DEVICE AND METHOD

RELATED APPLICATIONS

This application claims benefit of priority from U.S. 60/701,263, filed Jul. 21, 2005, the contents of which are incorporated herein by reference.

BACKGROUND OF THE INVENTION

The plasma membranes of all cells are bilayered and carry a net negative charge at the inner layer and a net positive charge at the outer layer, which is affected by the flow of ions in and out of the cell. When the voltage potential (net difference in electric charge across the membrane) of a cell is zero, the cell dies. In addition, nerve cells receive and send chemical signals that create electrical action potentials for rapidly signaling other neurons and muscle cells. Thus, physiological function is regulated, in part, by electrical properties.

A corona is a process by which a current develops from an electrode with a high potential in a neutral fluid (such as air), by ionizing the fluid to create a plasma around the electrode. The ions generated will pass charge to adjacent areas of lower potential. Coronas produce ozone in air and corona discharge is used commercially to manufacture ozone.

While a number of methods and devices are known for applying electrical current to parts of the human body to alleviate pain, speed healing, and/or relieve disease symptoms, improved methods and devices are still desirable.

SUMMARY OF THE INVENTION

The invention described comprises a system for treating a medical disorder in a patient in need thereof comprising a source of variable AC voltage having a frequency in a range of about 10-100 kHz and a voltage in a range of about 500-2000 volts, and one or more glass electrodes connected to the source, wherein at least one glass electrode is shaped to treat a particular tissue or disorder, and the system is sized such that the one or more glass electrodes emits a corona discharge when applied to an area of the patient and energized with the variable AC voltage, wherein the source of variable AC voltage is adapted to apply the variable AC voltage at a constant frequency during energization of the electrode with the variable AC voltage.

BRIEF DESCRIPTION OF THE DRAWINGS

FIG. 7 is drawing of an F3 type glass electrode showing dimensions.

FIG. 8 is a drawing of an S2 type glass electrode showing dimensions.

FIG. 16 is a circuit diagram of a 120 V, variable DC Voltage supply for use in the system depicted in FIG. 1.

DETAILED DESCRIPTION OF THE INVENTION

The invention provided herein is an electrical system, referred to as a "corona system," and a method for using the corona system in the treatment of medical disorders and in the improvement of site-specific drug delivery. The hypothesized mechanisms of action for the treatments are (1) stimulation of blood circulation in the affected area by relaxing blood vessel constriction; (2) an increase in extracellular molecular energy in the area of application; and (3) creation of ozone, which has an antibiotic effect, in the vicinity of the electrode.

Electrical Components

Figure 1:
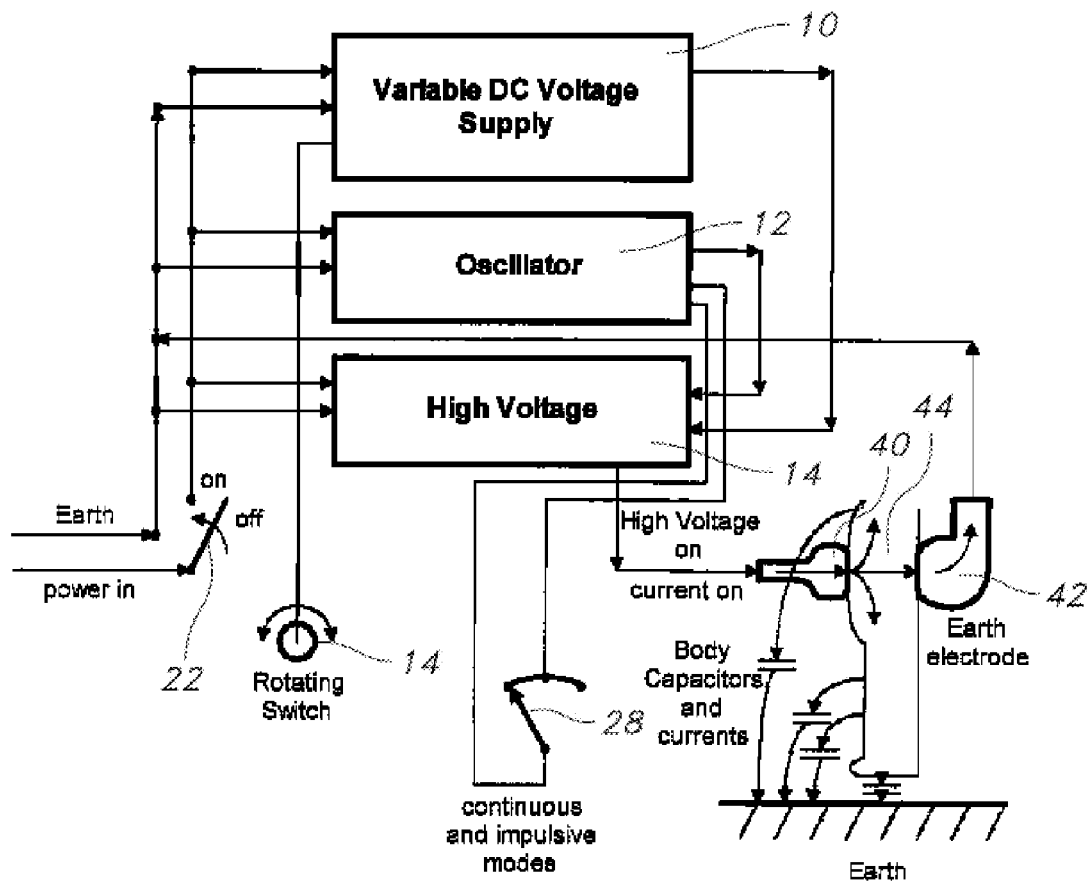
FIG. 1 is a schematic diagram of the components of the corona system.

The corona electrical system is designed to produce a variable sinusoidal voltage waveform having a maximum amplitude of 2000 V, a frequency of about 25,000 Hz, and a maximum output current of 30 mA. As shown in FIG. 1, the electrical equipment includes a variable DC voltage supply (10), an oscillator (12), and a high voltage device (14), each of which is now described.

Variable DC voltage supply (10) receives an alternating-current voltage input ("power in"), chops the voltage input, rectifies the chopped voltage signal, and applies the rectified voltage signal to a capacitor to obtain a variable DC voltage. The variable DC voltage is then supplied to a high voltage device (14), which is described below.

Oscillator (12) is designed to produce a variable sinusoidal voltage waveform which is supplied to high voltage device (14). Oscillator (12) may operate in either a "continuous" mode or in a "burst mode." In the continuous mode, oscillator (12) provides a continually oscillating voltage waveform, and, in an exemplary embodiment, provides a voltage waveform having a maximum amplitude of 2,000 V, a frequency of about 25,000 Hz (25 kHz), and a maximum current of 30 mA. Although an exemplary frequency of about 25 kHz and exemplary maximum voltage of 2000 V is discussed herein, the frequency may be in a range of 10-100 kHz and the voltage in a range of about 500-2000 Volts. The maximum current is limited by the frequency of the voltage and the tolerance of the human body, which has been calculated. For example, for a frequency of 60 Hz, the tolerance limit is 5 mA; for 11,000 Hz, the tolerance limit is 30 mA, and for a frequency of 100,000 Hz, the tolerance limit is 500 mA. See Standard Handbook for Electrical Engineers, D. G. Fink and J. M. Carroll, Eds., McGraw-Hill, New York, 1968, Section 29-14. In general, for safety, the corona system employs a current that is approximately half of the tolerance limit. To calculate a useful current for the frequencies applied with the corona system the following formula is applied: $I=(0.03\times F^2)+(2\times F+5)$, where I is the current in milliamps and F is the frequency in kHz. In the burst mode, oscillator (12) switches between providing an oscillating output and a non-oscillating, zero voltage output. As a non-limiting example, in a quick burst mode, oscillator (12) alternates between providing an oscillating output for 10 milliseconds and a non-oscillating, zero voltage output for 10 milliseconds. In a slow burst mode, the period of oscillation or non-oscillation increases to 35 milliseconds. Voltage waveforms for the continuous, quick burst and slow burst modes are illustrated in FIG. 2*a*.

Again referring to FIG. 1, high voltage device (14) receives the variable DC voltage (produced by variable DC voltage supply (10)) and the oscillating voltage waveform (produced by oscillator (12)) and produces a high-voltage AC signal with a frequency of 25 kHz. High voltage device (14) provides the high-voltage AC signal to glass electrode (40). A series of glass electrodes, optimized for particular treatments, are used to apply a voltage to specific areas of the body of a patient, hence delivering current to particular tissues and organs for treatment.

Figure 13:
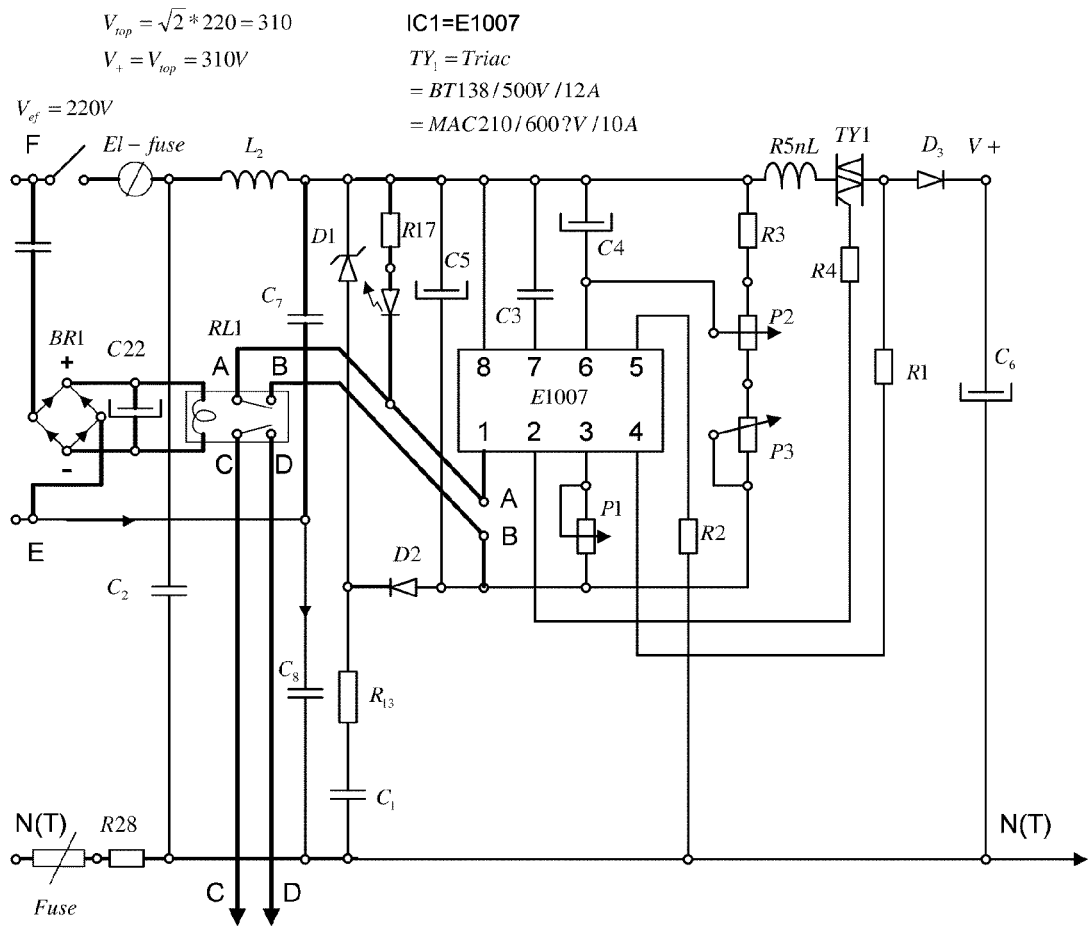
FIG. 13 is an exemplary circuit diagram of a 220 V, variable DC Voltage supply for use in the system depicted in FIG. 1.
Figure 14:
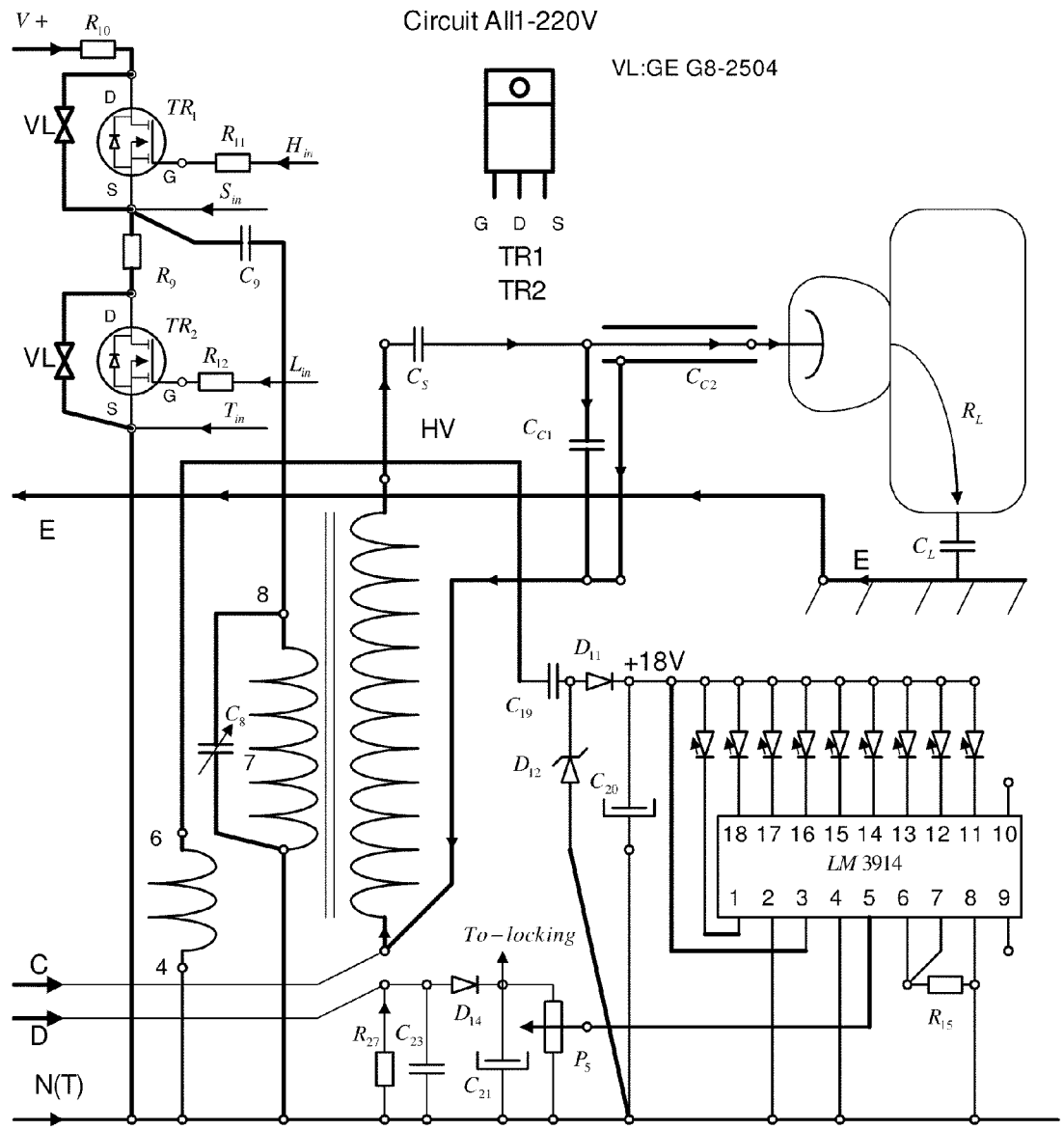
FIG. 14 is an exemplary circuit diagram of a 220 V, high voltage power supply for use in the system depicted in FIG. 1.
Figure 15:
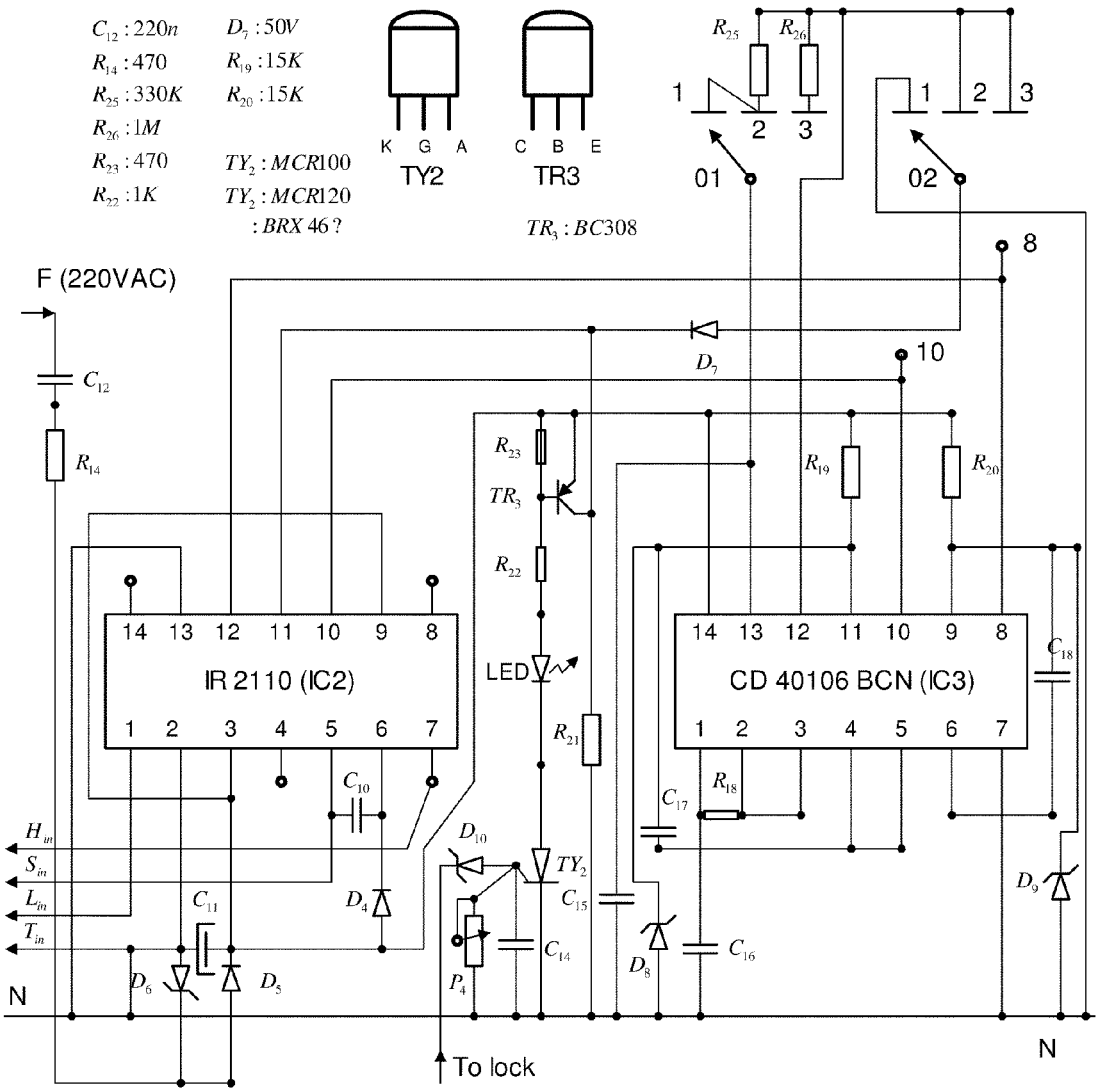
FIG. 15 is a circuit diagram of a 220 V, oscillator including a switch for continuous and impulsive mode operation of the system depicted in FIG. 1.
Figure 17:
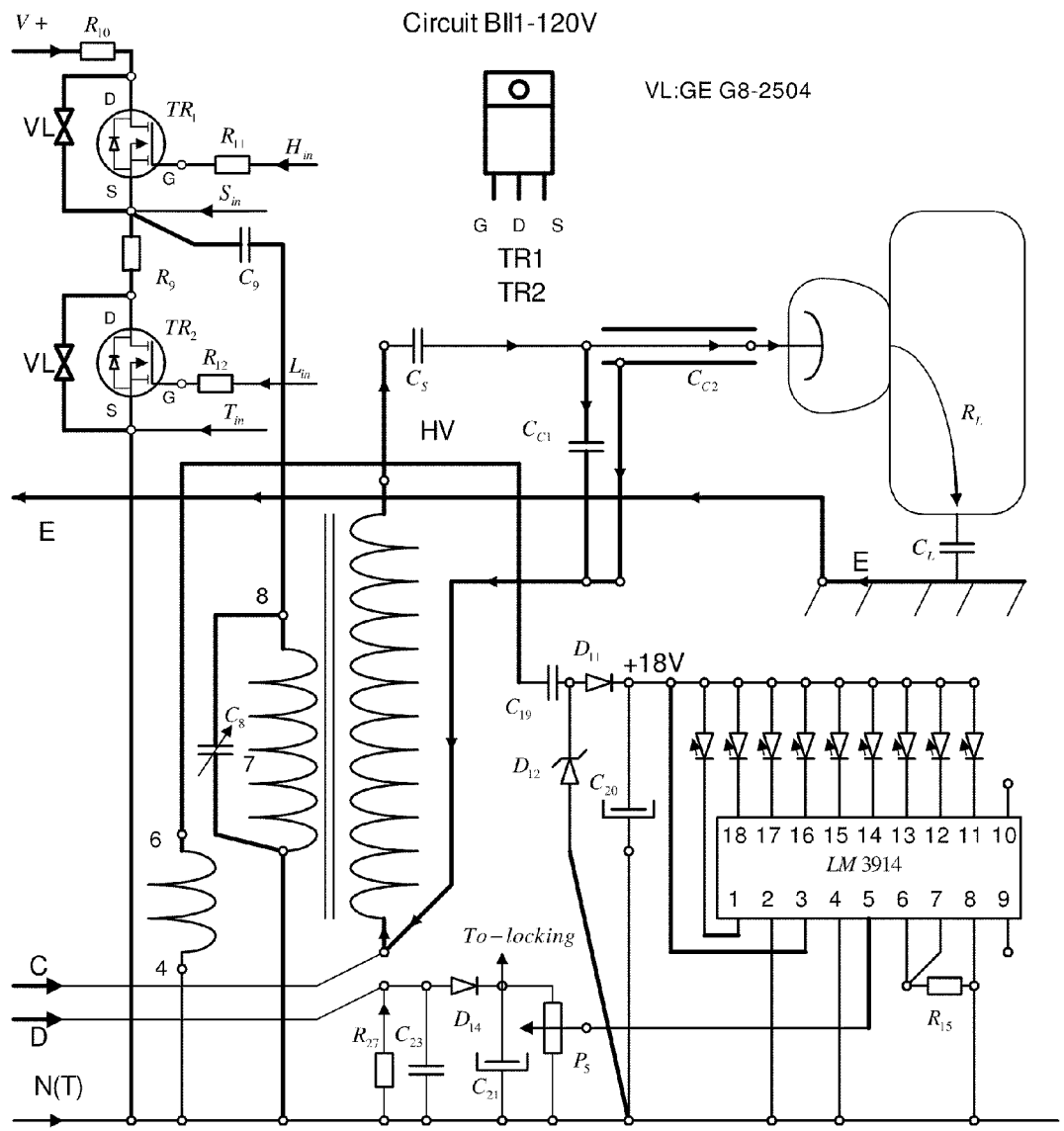
FIG. 17 is a circuit diagram of a 120 V, high voltage power supply for use in the system depicted in FIG. 1.
Figure 18:
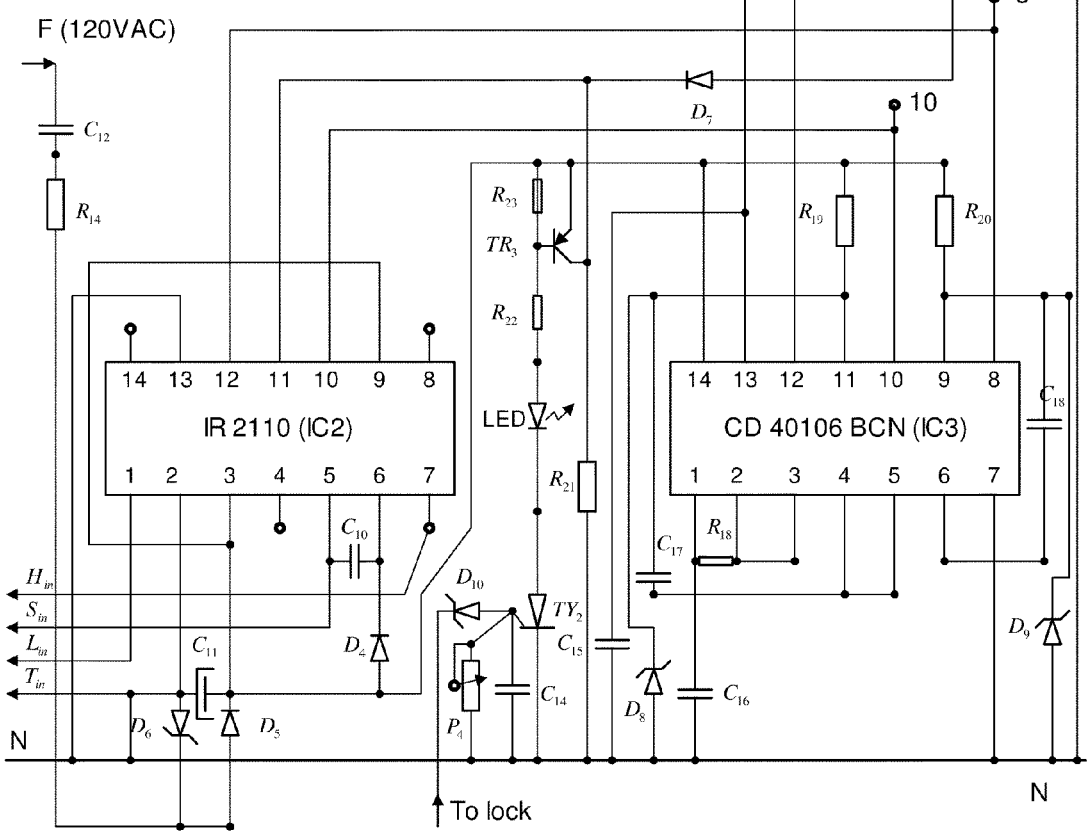
FIG. 18 is a circuit diagram of a 120 V, oscillator including a switch for continuous and impulsive mode operation of the system depicted in FIG. 1.

Exemplary embodiments of the system components are shown FIGS. 13-18. FIGS. 13-15 show details of the Variable DC Voltage Supply 10, the Oscillator 12 and the high voltage source 14 implemented for an input power supply of 220 V 50 Hz, as is typical in Europe, while FIGS. 16-18 show the same system components but for use with a power supply of 120 V, 60 Hz typical of the power supply in the United States.

Figure 2:
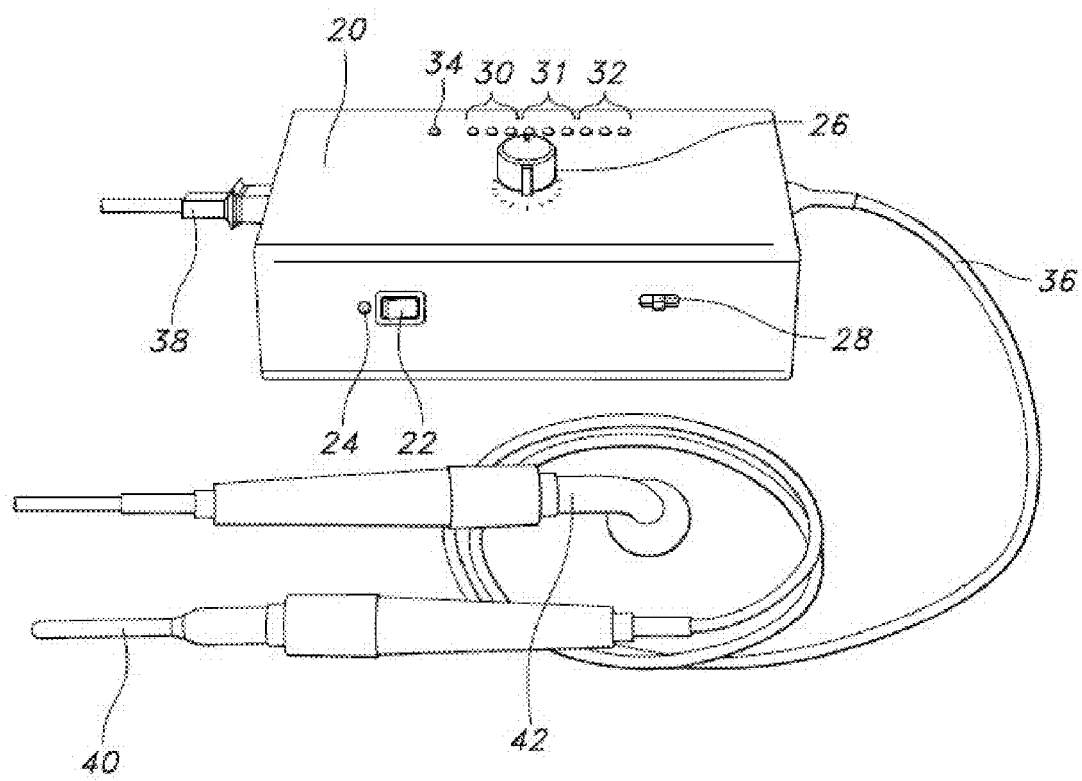
FIG. 2 is a photograph of a prototype of the corona system.
Figure 2A:
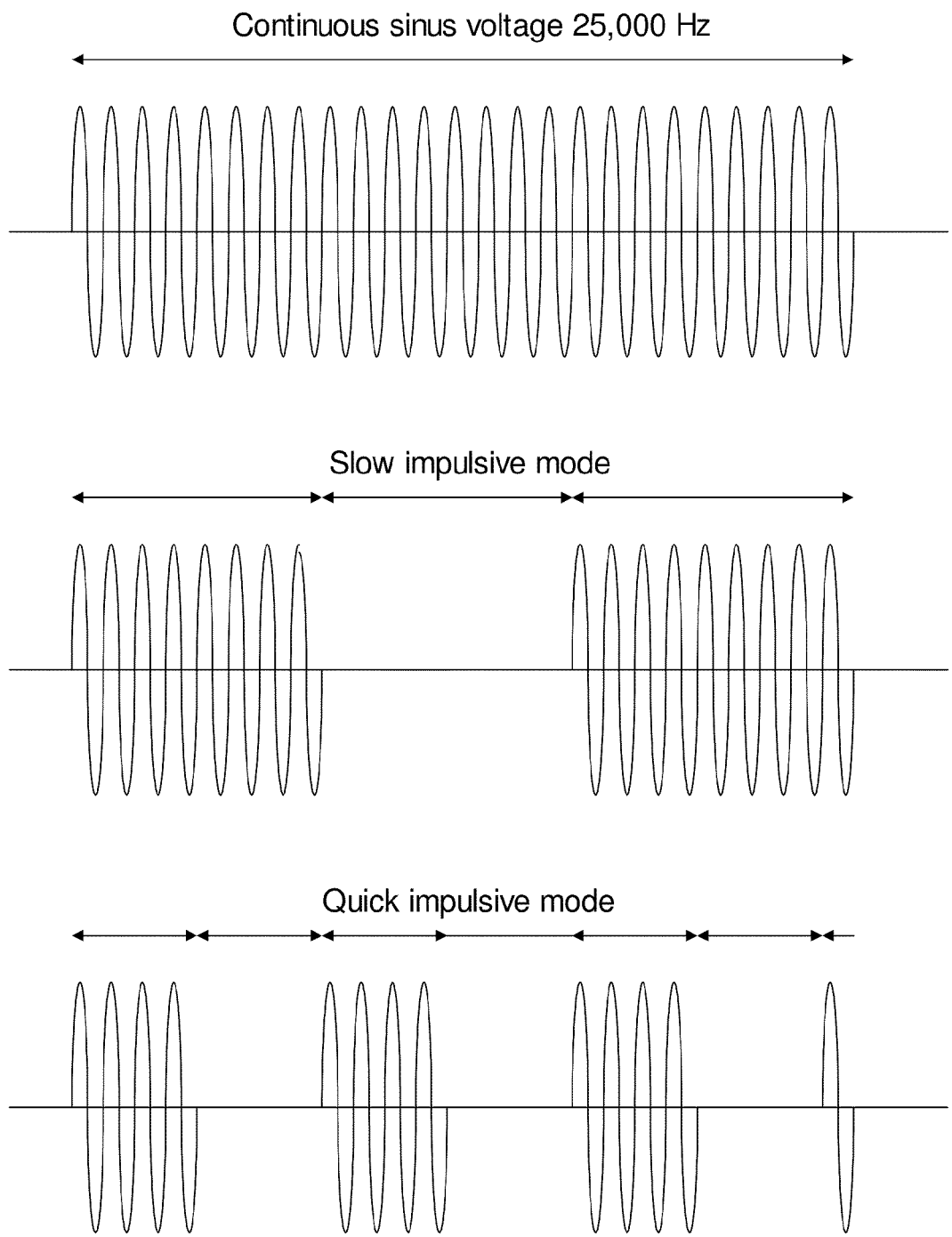
FIG. 2a is a depiction of the sine waves for modes of use of the corona system.

The system is contained in a housing (20), shown in FIG. 2. The housing provides a power switch (22) (also in FIG. 1) to activate or deactivate the external power supplied to the system; a red LED (24) to indicate that the external power to the system is activated; a rheostat (26) (also in FIG. 1) to control the voltage level provided by the variable voltage supply (10 in FIG. 1); a linear switch (28) (also in FIG. 1) to regulate whether the voltage is supplied continuously, in quick burst, or in slow burst mode; a series of nine LEDs (30-32) to indicate the level of current being applied, three LEDs each of green (30) (indicating low current), yellow (31) (indicating intermediate level current), and red (32) (indicating high current); a security lock that cuts off the voltage if the maximum safe current level is exceeded and an indicator for the status of the security lock (34); a shielded power cord (38); and electrical connections (36) for the electrodes (40, 42). Once the security lock has been activated, the electrode must be removed, the voltage decreased, and the power switch turned off and then on again to restore power to the electrode. The system may be used with either a single electrode or with two electrodes in tandem. FIG. 1 shows the application of two electrodes, an "active" electrode (40) connected to the output of the high frequency voltage source and a grounded ("earth") electrode (42) across an area of edema on the patient's body (44), for example across a knee, an arm, or a finger.

Figure 3:
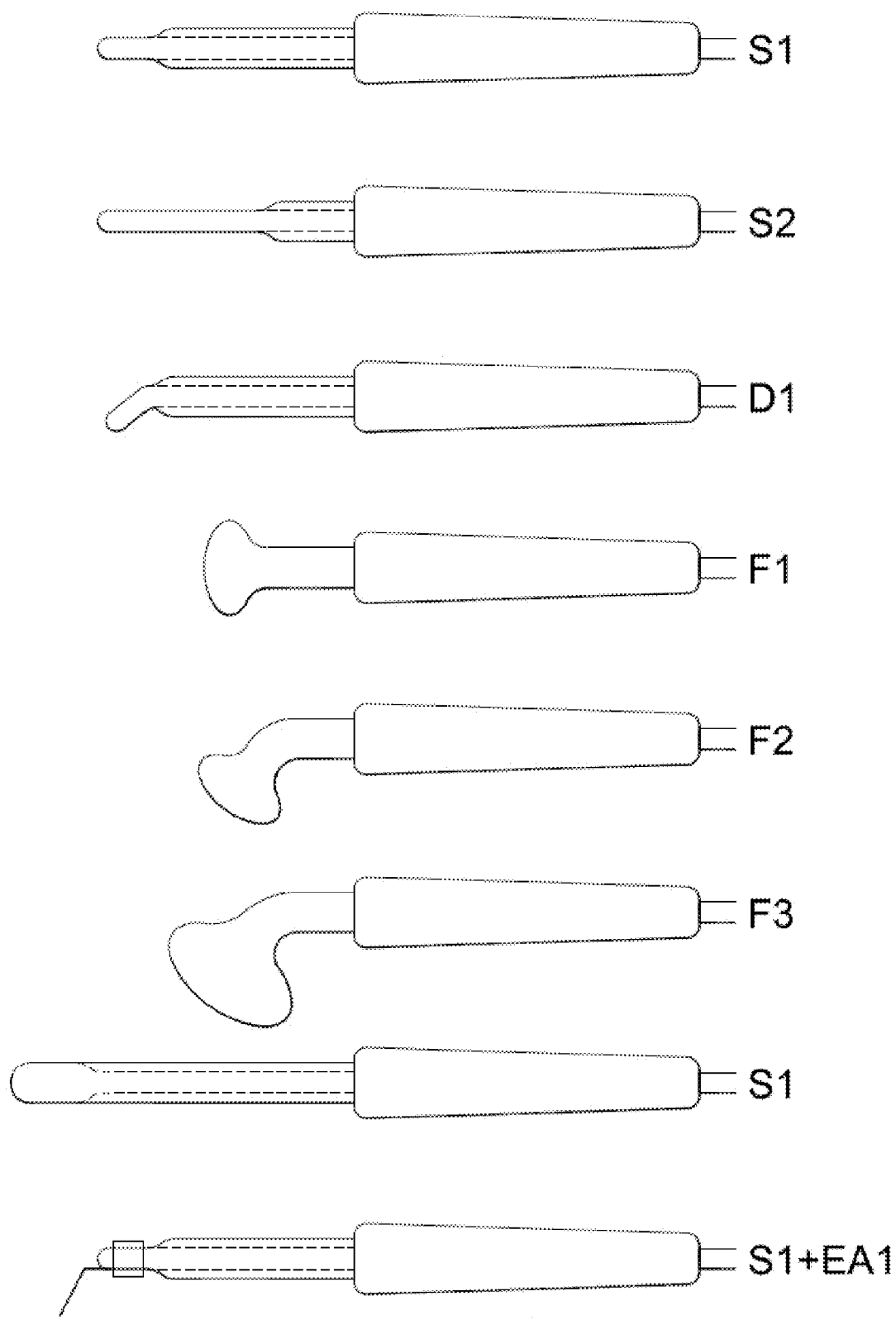
FIG. 3 is a drawing of different shapes and types of electrodes for use with the corona system.
Figure 4:
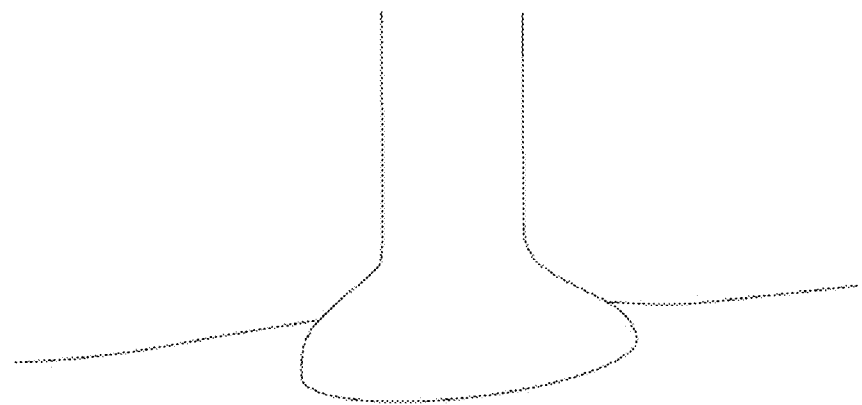
FIG. 4 is a photograph of an electrode applied to a surface.
Figure 9:
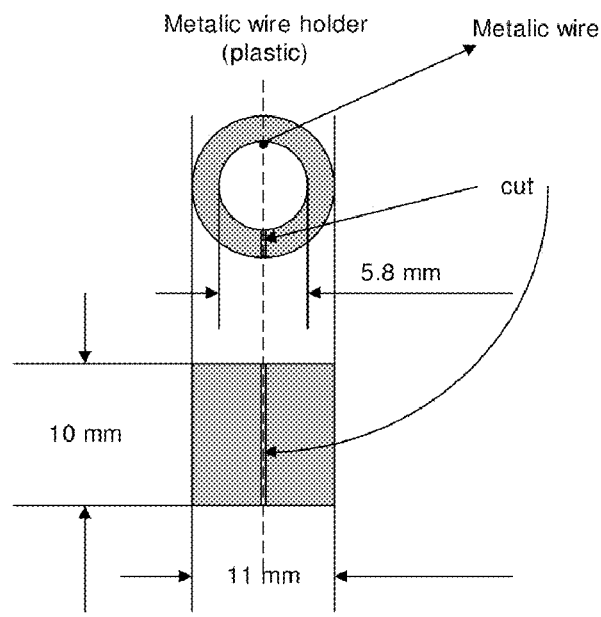
FIG. 9 is a drawing showing a cross section of a plastic, metal wire holder that can be used with the electrode.
Figure 5:
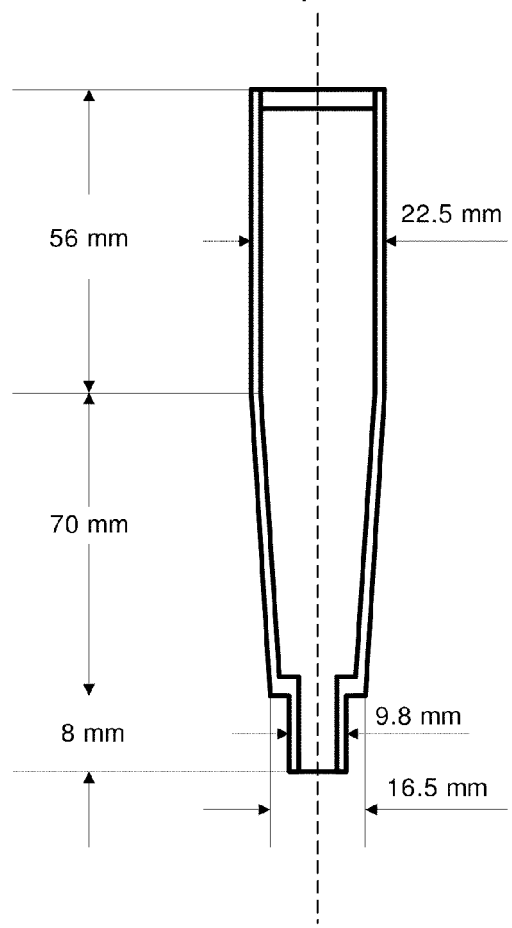
FIG. 5 is a drawing of an electrode handpiece showing dimensions.
Figure 6:
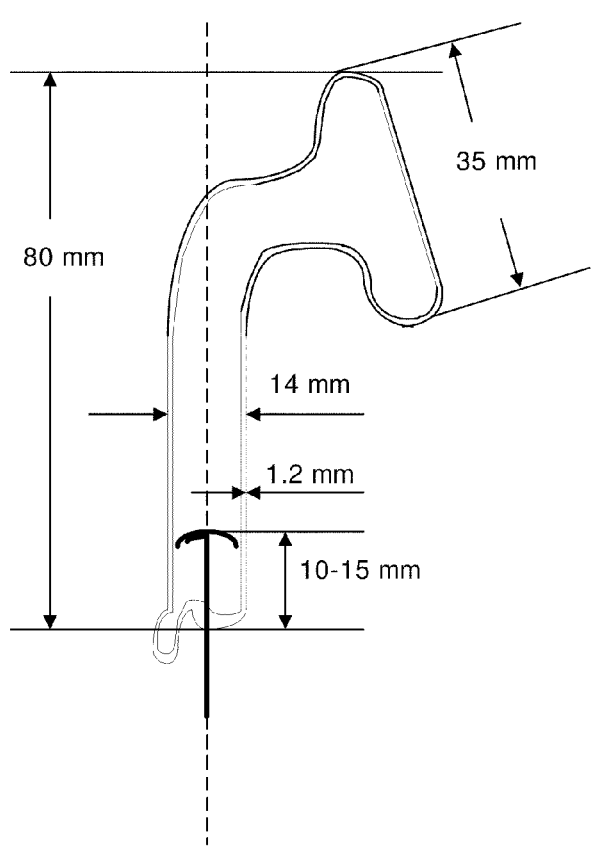
FIG. 6 is a drawing of an F2 type glass electrode showing dimensions.
Figures 10, 11, 12, 12B:
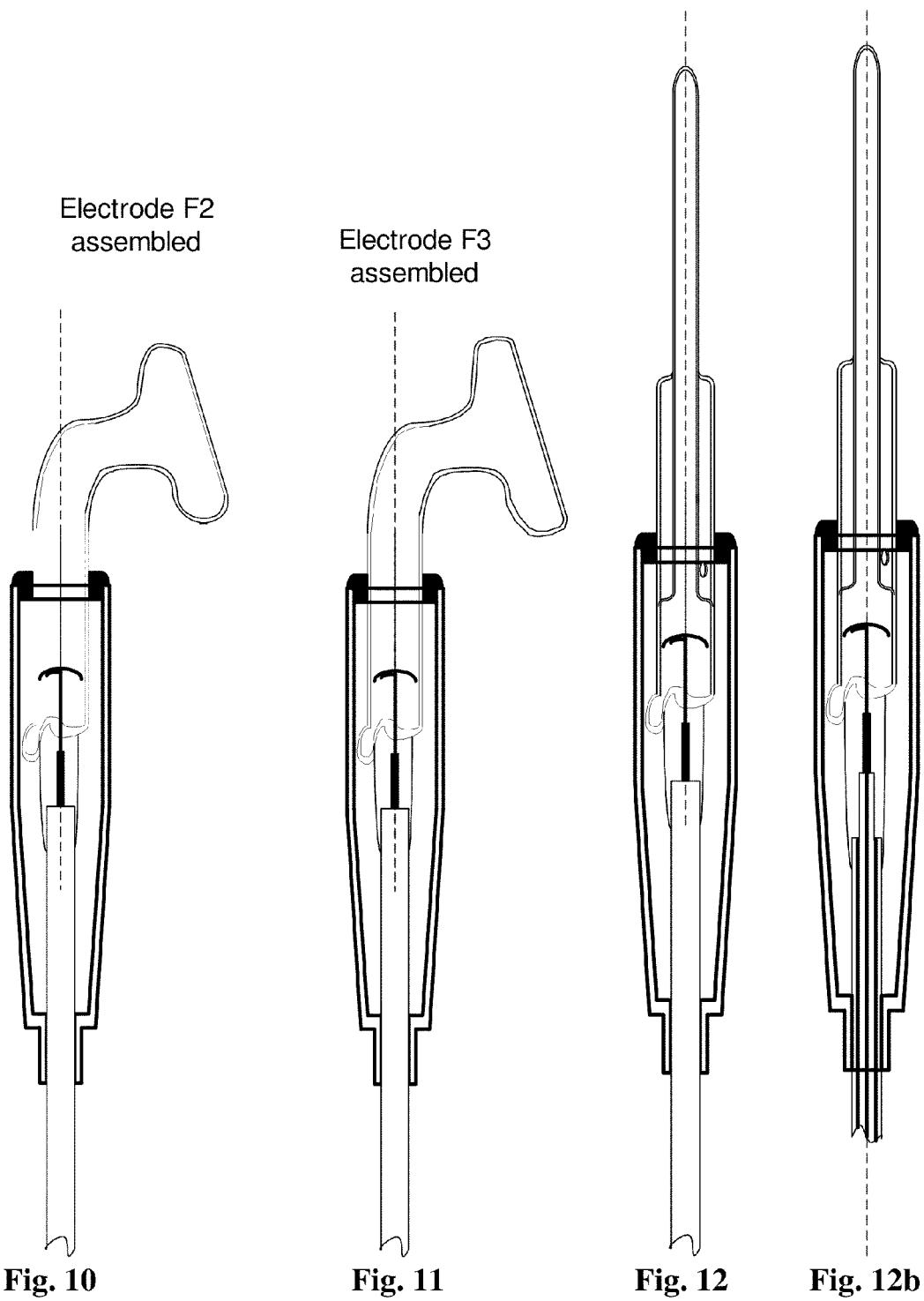
FIG. 10 is a drawing of an F2 electrode assembled in a handpiece.
FIG. 11 is a drawing of an F3 electrode assembled in a handpiece.
FIG. 12 is a drawing of S2 electrodes assembled in a handpiece.
FIG. 12b is a drawing of an S2 electrode with a shielded cable.

A series of different types of electrodes, S1, S2, D1, F1, U1, and S1+EA1, which are referred to in the Examples, is shown in FIG. 3. FIG. 4 shows an exemplary glass electrode being applied to a surface. FIG. 5 shows one embodiment of a handpiece for an electrode and dimensions for the handpiece. FIGS. 6-8 illustrate F2, F3, and S2 type glass electrodes with their dimensions. FIG. 9 shows a specialized holder for a metal wire to be used with an electrode such as S1 in FIG. 3 to modify the electrode for special applications, for example, dentistry. FIGS. 10-12 illustrate F2, F3, and S2 electrodes assembled with the handle. The S2 electrode in FIG. 12*b* has a shielded cable.

Electrodes

The shape and construction of the glass electrodes depends on where they will be used. For the purposes of this disclosure, the tip of the electrode that is the point of contact with the tissue to be treated is referred to as the "application region," and the remainder of the electrode that is structural or insulating, is referred to as the "structural region". Electrodes used in the mouth, anus or vagina have double glass insulations in the structural region to protect tissues surrounding the area where voltage is applied (S1, S2, D1, U1, and S1+EA1 in FIG. 3). The application region is shaped to optimize treatment of a particular area or tissue type. As shown in FIG. 3, the application region may be tubular and shorter than the structural region (S1, for use in the ear), tubular and longer than the structural region (S2, for use on convex surfaces, e.g., arm, leg, nose), tubular and positioned at an angle to the structural region (D1, for use in dentistry and treatment of the mouth), spatulate (U1, for use in the mouth, vagina, or anus), or bulbous with an outer surface that contacts with the skin or mucosa of a patient, that is flat, convex, or concave (F1, F2, F3, for surface applications, e.g., hands, feet, chest, back, neck). The F3 electrode in FIG. 3 is designed for use as a grounded electrode. The electrodes may also be modified by affixing a wire to the application region (e.g., S1+EA1, for use in dentistry). Construction of the "mushroom type" electrode (F1-F3, in FIG. 3) is representative of one method of electrode construction and will now be described.

Referring now to the glass electrodes shown in FIGS. 6-8, components of the electrodes include thin nickel chromium plates 62 and kovar alloy wire 64 for the metallic electrode; electron tube glass tubes 66 of different diameter and thickness; and in the corresponding assembled electrode configurations shown in FIGS. 10-12*b*, plastic handles 68 formed by molding (shown also in FIG. 5); a shielded cable 120 for double electrodes; an insulated cable 100 for single electrodes; and plugs (not shown) for the two types of cables. The thickness of the final glass electrode is preferably about 1-2 mm.

For manufacture of the glass electrodes, first, the outer side 61 of the nickel chromium plate is sand blasted, then the plate is cut circularly and shaped semi-spherically as shown in FIGS. 6-8 and 10-12*b*. The kovar wire is cut, shaped, and welded to the nickel chromium plate with point welding.

The glass tubes are shaped at high temperature, by blowing and using templates. The metal electrode is assembled at the bottom of the glass piece, and sealed inside the glass at high temperature. A small tube is then connected to the bottom of the glass electrode at high temperature.

A vacuum is applied through the small tube to remove air and then the tube is used to fill the electrode with an inert gas. After filling, the tube is closed by melting the glass, leaving nub 70 shown at the base of the electrodes in FIGS. 6-8. When the electrode is energized, the inert gas is ionized, causing a relatively small voltage drop across the ionized gas and a relatively larger voltage drop caused by passing through the thickness of the glass of the electrode. Glass thickness may be optimized to provide adequate strength and voltage drop.

A cable is inserted from the bottom of the plastic holder and welded to the kovar wire of the glass electrode and the exposed wire is insulated. The base of the glass electrode is placed in the plastic holder and fixed to the holder with adhesive. An appropriate plug or connector is connected to the free end of the cable.

The shape of the glass electrode can be optimized for treating different organs or tissues. An electrode may be used alone or with a second, grounded electrode. Current frequency and voltage may be varied to optimize the treatment.

The corona system of the present invention has many uses, including treatment of medical disorders including burns, lesions, wounds, neurological disorders, disorders of the intestinal tract, genito-urinary tracts, and internal organs, orthopaedic disorders, ear nose and throat disorders, dermatological disorders, dental disorders, relief of cold and flu symptoms, and relief of pain. Examples of treatments for specific disorders and diseases in each of these categories are provided in Example 4. In addition the method may be used to increase drug delivery at the site where the drug is needed. For example, chemotherapy agents may be delivered more effectively to the tumor area so that the total amount of chemotherapy agent may be decreased, or antibiotics delivered systemically may be concentrated at the site of infection.

Physiological Effects

The method of the invention is believed to act on tissues through the following mechanisms, however, use of the invention is not limited to these proposed mechanisms of action.

(1) Dispersing Edema and Improving Blood Circulation

Edema is part of the inflammatory response and occurs as a result of many injuries, infections, and diseases. In many instances, the edema is the source of pain. When the edema is dissipated, blood circulation in the affected area improves. For example, the glass electrode of the invention may be applied to a fresh burn to remove the edema and relieve pain. For surface applications, a single electrode may be used. To treat internal edema, two electrodes are applied.

While not committing to any particular mechanism of action, it is believed that because blood circulation is decreased when blood vessels contract in response to increased intra- and extracellular levels of calcium ions, electrical stimulation in the ranges reported in accordance with the present invention act to disperse calcium ions, relax blood vessels, and improve circulation in the area of the applied electrical stimulation. As a result of the improved blood circulation in the affected area, medication administered systemically can more readily reach the affected site, and provide treatment of the affected area more quickly. While the exemplary voltages and frequencies discussed herein are believed to facilitate this mechanism, any voltage or frequency that facilitates this mechanism may be beneficial. Similarly, the use of voltages or frequencies within the claimed ranges are not limited to producing a beneficial result by any particular mechanism.

When a charged electrode is applied to a tissue with edema, the current within the tissue increases. Thus, the corona system can be used to detect the sites of edema in the body, as well as to treat the edema. In the system described herein, there are 3 green, 3 yellow, and 3 red LEDS that indicate the relative current level, but the current may instead or also be monitored with traditional analog or digital gauges of any kind. When an electrode is moved from an area with no edema to an area with edema, an increase in current is detected and indicated by the colored LED indicators.

As the electrode is moved across areas of the body, the current may increase for one of two reasons: either there is edema, or the electrode is positioned over a different type of soft tissue. The possibility of having encountered a different type of soft tissue can be ruled out, for example, by checking a similar type of tissue on the other side of the body, or when it is known that the electrode is still positioned over the same type of tissue that produced the lower reading. So, for example, a charged electrode may be applied on the back of a patient at the left bottom lung and the grounded electrode applied from the chest at the bottom lung and the current checked. The same may then be done for the right bottom lung. An increased current on one side relative to the other indicates an edema on the high-current side. The same procedure can also be carried out using only a single electrode, but the observable current difference is typically less than with two electrodes.

(2) Energizing Molecules in Extracellular Fluid

Application of the current, oscillating with, for example, a frequency of 25 KHz, to tissues energizes ion pairs in the extracellular fluid and increases molecular mobility. As ions collide, adjacent molecules become energized. This effect can be used to disperse accumulated or deposited material in extracellular spaces that give rise to disease conditions. Such conditions include kidney stones, amyloid plaques, and accumulation of sugar in diabetes.

(3) Producing Ozone for Surface Sterilization

When the glass electrode is applied to skin or mucosa, a corona discharge is produced that creates low energy, harmless ultraviolet waves. Ultraviolet waves break oxygen molecules and convert oxygen to ozone. Ozone acts as an antiseptic to destroy bacteria and viruses on tissue surfaces. The amount of ozone is localized to the site of electrode application and is limited (about 0.15 ml in 20 minutes), but provides localized sterilization of the site.

This property is particularly useful for channel sterilization in dentistry. A thin metallic piece may be affixed to the glass electrode, for example with the wire holder shown in FIG. 9, and applied to the channel drilled in the tooth. See FIG. 3, S1+EA1.

(4) Restoring Sensory Functions to Skin

When sensory nerve receptors are damaged, the skin loses sensations of hot or cold or touch. These sensory functions may be restored by using the applied current to stimulate sensory receptors directly.

EXAMPLES

1. Effect of the Corona System on Induced Edema

Human subjects were injected on the inside of the forearm with compound 48/80 (10 ug) at two sites to induce an inflammatory reaction and edema. After edema developed at both sites (2-3 min), a 25 kHz signal was applied through a surface electrode to one injection site for 15 min. Edema at the treated site was almost completely dissipated within minutes, whereas edema at the untreated site was unaffected.

2. Effect of the Corona System on Burns

Thirty-two patients with burns were treated with a corona discharge system in the area of the burn. Another thirty-two patients with burns were treated with silver nitrate over the burn and served as a control group. In the corona discharge treated group, burns healed in 13 days, whereas, in the control group, burns did not heal until 18 days. Microbiologic results were also better in the corona-treated group: for the duration of the therapy, the corona treated group had only 2 patients (6.3%) with infection at the wounds, whereas the control group had 7 patients (21.8%) with such infections. While not being bound to any particular mechanism, it is believed that the lower rate of infection in the corona-treated group is the result of the ozone generated by the corona. The differences in results between the two groups was statistically significant. The difference between the two treatments was statistically significant.

3. General Use of the Corona System

The single electrode system can be applied by the patient or by another person. The double electrode system should be applied by another person. The patient should be isolated from ground (as shown in FIG. 1), e.g., not contact the floor with bare feet, or be in contact with metal items, and other persons should not touch the patient's skin during application of the system.

To use the system, the power switch of the equipment must first be in the off position. The plug of the selected glass electrode is fitted into the electrode outlet on the equipment box. The rheostat is turned to the minimum position. The power switch can then be turned on.

The patient's skin or mucosa is contacted lightly with the glass electrode, and then moved slowly or pushed lightly against the skin or the mucosa for some seconds. During application of the electrode, the system is operated at constant frequency. The electrode can then be lifted and applied at another point as necessary. The current may be applied for 5-6 minutes to a small area such as a finger or a small region of skin; for up to 10 minutes for an area of 5×5 cm; and for up to 20 minutes for larger areas. The total maximum period of use should be limited to 20 minutes per day, even if the electrode is applied to different areas of the body. If necessary, the total application period per day can be increased to 25-30 minutes for a few days for acute cases.

The system may be used for a maximum of 20 serial applications, daily or every other day, which are followed by a non-application-period of one month before a second application is made. If longer periods of treatment are needed, cycles of application for one week followed by non-application for one week should be used.

The system is used in continuous mode if the heat from the electrode does not disturb the patient. Burst modes are used if heat disturbs the patient, and slow burst mode is preferred in this case.

Colored LEDs on the box indicate the intensity of voltage being applied. Intensity may be adjusted with the rheostat. In general, only low intensity is used for infants and young children. The intensity should be adjusted so that the patient is comfortable and does not feel pain due to application of the system. Higher intensity may be used in acute cases. Details of intensity adjustment are given separately for each application described in the Examples.

If the equipment is applied with too high intensity, the security lock automatically shuts off the power. This security system protects the patient from current levels that are above the maximum defined current level. If the security lock is activated, the glass electrode should be removed from the patient's body; the rheostat should be turned to the minimum position, and the power switch can then be turned on again.

4. Specific Applications of the Corona System (1) Improvement and Targeting of Drug Delivery The invention provides a method for increasing blood circulation in a localized area of the body of a patient. Voltage is applied through the glass electrode to the skin or mucosa adjacent to the area to be treated at constant f. As a result, blood circulation is stimulated in that area, and systemically administered drugs will be delivered to the area more rapidly and in a higher concentration.

This treatment may be particularly useful in chemotherapy applications, as cancer tumors are characterized by low blood circulation and edema. As a result, the majority of a systemically administered chemotherapeutic agent is spread throughout the body. Other tissues may be damaged by the agent and the amount of agent actually reaching the tumor is diminished.

The corona system may be applied for 20-30 minutes, beginning 5-10 minutes after administration of the chemotherapeutic agent. For internal organ tumors double electrodes are used, while a single electrode is used for skin cancers. By increasing the amount of agent that reaches the tumor, it may be possible to reduce the total amount of agent administered to the patient, thus reducing damage to healthy tissues. Use of the corona system will similarly allow the administration of many therapeutic compounds at lower doses.

(2) Dermatological Treatment (a) Facial Wrinkles

An appropriately shaped surface electrode, such as F1, F2, or F3 in FIG. 3, is selected and used at low or medium intensity on the affected area in continuous mode or slow burst mode. Treatment is daily or every other day for 5-10 minutes. Course of treatment is 5-10 procedures. When applying the electrode on the skin close to the eyes, the eyes should be closed.

(b) Premature Baldness, Alopecia Areata

A surface electrode is used at low intensity and is slowly moved from the forehead to the back of the head along the scalp. Each procedure lasts for 5-10 minutes, daily or every other day. Course of treatment is 15-20 procedures.

(c) Local Pruritis

A surface electrode is used at low intensity and is moved along the surface in longitudinal or circular movements in affected areas. Each procedure lasts for 5-10 minutes, daily or every other day. Course of treatment is 10-15 procedures. In case of itching in the anal passage, the procedure is performed with a straight electrode.

(d) Chronic Limited Neurodermatitus (Lichen Simplex Chronicus)

A surface electrode is used at medium intensity and is moved in longitudinal or circular movements along the lesion. Each procedure lasts for 5-10 minutes, daily or every other day. Course of treatment is 10-15 procedures.

(e) Chronic Eczema

A surface electrode is used at medium intensity and is moved in longitudinal or circular movements along the affected area. Each procedure lasts for 5 minutes, daily. Course of treatment is 10-15 procedures.

(f) Dermatitis, Contact Dermatitis, Furuncle, Ecthyma, Fungal Infections of Skin and Nails, and Warts A metallic wire with a plastic holder can be connected at the tip of the electrode (see exemplary electrode S1+EA1 in FIG. 3 and exemplary wire holder in FIG. 9) to create further applications. The modified electrode functions as a micro-coagulator when used for one minute, as a micro-cutter when used for 2 minutes, and as an ozone producer to sterilize a surface when used for 3-5 minutes. An electrode with this modification can be used to destroy fungus on the skin and to sterilize the area with ozone. The modified electrode can also be used once a week for 3-5 minutes to treat warts.

(3) Surgical Treatment (a) Burns, First Degree and Second Degree

In the case of burns, all basic physiological effects of the equipment are utilized. Edema is dispersed to hinder loss of blood plasma, circulation is improved, and tissue regeneration begins immediately. When the pressure from the edema is relieved, pain is also diminished or relieved. Ozone production sterilizes the burned area, helping to fight infection in the region of the burn.

A surface electrode is applied in slow burst mode directly on the burned area, starting with the area just outside the burn. Low intensity voltage is used at the beginning of treatment and may be increased depending on the comfort level of the patient. The treatment is applied for 15-20 minutes daily. Course of treatment is 5-20 procedures.

(b) Surgical Lesions

The equipment can be applied on a surgical lesion as soon as possible after the operation to decrease edema, minimize scarring and pain, and accelerate healing. Ozone acts to sterilize the area of application.

The shape of the surface electrode is selected based on the geometry of the lesion. The electrode is used in slow burst mode at medium intensity. Intensity may be increased depending on the comfort level of the patient. Treatment is 5-20 minutes (as required), daily. Course of treatment is 5-10 procedures.

(c) Hemorrhoids

Treatment should be performed after acute incidents. In case of anal fissure and sharp pain a suppository with belladonna may be inserted into the straight intestine 15 minutes before the procedure.

Before the procedure the patient should empty the intestines and wash the perineal area with warm water. The patient lies on his side with his legs touching the belly. A special anal electrode, such as U1 in FIG. 3, is coated with a lubricant and inserted into the straight intestine 4-6 cm deep. The position of the electrode holder is fixed so that electrode lies horizontally and does not press the lateral wall of the intestine. Intensity of the voltage is increased until the patient feels slight heat and is decreased when the heat is too high. The first treatment is 5 minutes. Thereafter, 2 minutes are added to each subsequent procedure up to a maximum of 15 minutes. The electrode is extracted only after the device is switched off. The treatment is performed daily or every other day. Course of treatment is 12-15 procedures.

(d) Phlebitis, Vein Thrombosis, Periproctitis

Treatment can be performed only after acute incidents. An electrode designed for internal use, such as U1 in FIG. 3, is applied to the straight intestine at a voltage intensity sufficient to give a feeling of slight heat. Treatment is 10-15 minutes daily. Course of treatment is 15-25 procedures.

(e) External Hemorrhoid Nodes

In the case of vivid external hemorrhoid nodes when it is impossible to insert a straight electrode into the straight intestine, a surface electrode, such as F1 in FIG. 3, is applied to the nodes. Voltage intensity is determined by a slight feeling of heat as described above. The treatment is for 3-7 minutes, daily. Course of treatment is 2-4 procedures.

(f) Chronic Prostatitis

An elongated straight electrode, such as S2 in FIG. 3, is coated with a lubricant and inserted into the straight intestine 8 cm deep to reach the area of the prostate. Low intensity voltage is used for 10-25 minutes, daily. Course of treatment is 15-20 procedures.

(g) Rectal Prolapse

A straight electrode, such as U1 in FIG. 3, is coated with a lubricant and is inserted into the into the rectum 4-5 cm deep. Low intensity voltage is applied for 10-25 minutes, daily. Course of treatment is 15-20 procedures. In children the procedure lasts for only 5 minutes, daily or every other day, and the course of treatment is 8-12 procedures.

(h) Obstructive Vascular Diseases

In the case of obstructive disorders of the vascular system, such as angiosplastic, thromboangistic and atherosclerotic disorders, a surface electrode is used at medium intensity and is moved longitudinally along the inside surface of lower and upper extremities. The treatment is for 10-12 minutes on each side (right and left limb), daily or every other day. Course of treatment is 10-15 procedures. At later stages of disease the electrode is applied to the lumbar sympathetic nodes. The electrode is operated at medium intensity and is moved from D10 to L4 paravertebrally from both sides. Treatment lasts up to 8 minutes per side, daily. Course of treatment is up to 15 procedures.

(i) Varicose Veins

At early stages of the disease a surface electrode is moved along expanded veins, at medium voltage intensity for 10-15 minutes, daily. Course of treatment is 15-20 procedures. An elastic stocking or bandage should be worn after treatment.

(j) Thrombophlebitis

Following acute inflammation, a surface electrode is moved along the veins, at medium voltage intensity, for 5 minutes, daily. Course of treatment is 10-15 procedures.

(k) Varicose Ulcers

Circular movements of a surface electrode are made along the skin about 7-10 cm from the center of the ulcer and along the ulcer surface while applying medium intensity voltage for 5-12 minutes. Subsequently, treatment is applied along the vertebrae at D10-L2, at medium intensity for 5-12 minutes for up to 15-20 procedures. X-ray and trophic ulcers are treated in the same way.

(l) Paraesthesia

In paraesthesia caused by lymphostasis a surface electrode is moved by longitudinal or circular movements on buttocks and thighs in the affected areas, at medium voltage intensity for 3-5 minutes, daily. Course of treatment is 15-20 procedures.

(m) Decubitus Ulcer (Pressure Sores)

In decubitus ulcer with low granulation development a surface electrode is moved in circular movements along the skin surrounding the ulcer at the distance of 7-10 cm from the center and on the ulcer surface. Subsequently, one can treat vertebrae from C5 to L2, at medium intensity, for 5-12 minutes, on days when the affected area is bandaged. Course of treatment is 15-20 procedures. The same method is used for treating wounds.

(n) Ankylosing Spondylitis (Bechterew's Disease)

A surface electrode is moved along the vertebral area (between paravertebral lines) from the neck to the coccygeal bone, at low voltage intensity for 8 minutes, daily or every other day. Course of treatment is up to 15 procedures.

(o) Phantom Pains

Phantom pains especially in phantom phenomena with neurotic symptoms in the post-operative period can be treated with a surface electrode moved over stump areas, at medium voltage intensity for 7-10 minutes, daily or every other day. Course of treatment is 12-15 procedures.

(4) Gynecological Treatment (a) Vulvitis

For chronic vulvitis a straight or surface electrode, such as F1, F2, or U1 in FIG. 3, is moved longitudinally along the vulva at low voltage intensity for 5-10 minutes, daily. Course of treatment is 10-15 procedures.

(b) Pruritis of External Genital Organs

A straight or surface electrode, such as U1, F1, or F2 in FIG. 3, is moved by longitudinal or circular movements along the external surface of genital organs and the internal surface of the upper thigh at medium voltage intensity for 5-10 minutes, daily or every other day. Course of treatment is 15 procedures.

(5) Treatment of Neurological Disorders (a) Acroparesthesia of Upper and Lower Extremities.

A surface electrode is moved by longitudinal movements along forearms and hands or from fingers to elbow, or on knee joints, or on feet and toes at medium voltage intensity for 3 minutes on each side, daily or every other day. Each successive procedure is increased by 1-2 minutes up to 10 minutes total. Course of treatment is 15 procedures.

(b) Symmetric Acrocyanosis of Upper Extremities

A surface electrode is moved longitudinally from fingers along the hand and arm surface, including the shoulder and also along the lower neck and thoracic region of the backbone, at medium voltage intensity for 7-10 minutes per each extremity, daily or every other day. Course of treatment is 15-20 procedures.

(c) Disorders Due to Occupational Vibration

A surface electrode is applied on forearms and hands at medium voltage intensity for 7-10 minutes per each side, every other day. Course of treatment is 10-12 procedures.

(d) Myositis

For treatment of acute myositis, a surface electrode is moved by longitudinal and circular movements on the injured muscle at medium voltage intensity for 5-10 minutes, daily or every other day. Course of treatment is 10-15 procedures.

(e) Myopathy

A surface electrode is applied to the area of injured muscles at high voltage intensity for 5-10 minutes, daily. Course of treatment is 15-20 procedures.

(f) Occupational and Repetitive Motion Disorders (e.g., Carpal Tunnel Syndrome)

Before starting the treatment, patient should cease the activity causing the disorder. In case of pain and paraesthesia in fingers, a surface electrode is applied to the forearms and hands, at medium voltage intensity for 7-10 minutes, every other day. Course of treatment is 10-12 procedures.

(g) After Effects of Cerebral Insult

Treatment may begin 1-1.5 months after the insult. A surface electrode is moved by longitudinal movements on injured extremities (surface where shoulder and forearm straighten or where thigh and knee bends), from fingers and along extremity surface including shoulder and pelvic girdle and also thoracic and lumbosacral regions of the backbone. Medium intensity voltage is applied for 10-15 minutes, daily or every other day. Course of treatment is 12-15 procedures. When both extremities are damaged, treatment is performed on both extremities in turn, and the course of procedure is up to 20 minutes.

(h) Lumbosacral Radiculitis

A surface electrode is moved by circular and longitudinal movements on affected areas, at medium intensity voltage for 5-10 minutes, daily. Course of treatment is up to 10-15 procedures.

(i) Shingles

For paraesthesia and itch caused by zone lichen, a surface electrode is moved by circular and longitudinal movements in the affected area, at medium voltage intensity for 7-10 minutes, daily or every other day. Course of treatment is 10-15 procedures.

(j) Raynaud's Disease

Raynaud's disease may be treated at all stages by applying a surface electrode at medium voltage intensity to the upper extremities for 7-10 minutes for each extremity, daily or every other day. Course of treatment is 15-20 procedures.

For lesions on lower extremities a surface electrode is moved upward from the toes along the whole surface including the lower-thoracic and upper-lumbar region of the backbone, for 10-12 minutes for each extremity, daily or every other day. Course of treatment is 15-20 procedures.

For trophic disorders the surface electrode is moved by circular movements on the ulcer surface, then along the vertebrae at D10-L2, for 5-12 minutes, on days when the affected surface is bandaged. Course of treatment is 15-20 procedures.

(k) Multiple Sclerosis, (MS)

A test is first made to determine if the treatment will be effective. An elongated electrode, such as S2 and F2 in FIG. 3, is applied to the neck of the patient for 5-10 minutes in slow burst mode, beginning at medium voltage intensity and moving the electrode along the neck. Intensity may be increased depending on the comfort level of the patient. If the patient feels sensation, such as heat, cold, itching, etc., in any area (even areas distant from the region where the electrode is applied), the electrode should be applied to those areas as in the test procedure.

The treatment may be used at any stage of the disease. For treatment of acroparaesthesia of the upper extremities, a surface electrode is moved by longitudinal movements upward from the fingers along the whole surface of the arm including the shoulder and also along the lower-neck and upper-chest region of the backbone. Voltage is applied at medium intensity for 7-12 minutes per each extremity, daily or every other day. Course of treatment is 10-12 procedures. For treatment of lower extremities, the electrode is moved from the toes upward along the whole leg surface, and along the lower-thoracic and upper-lumbar regions of the backbone at medium voltage for 10-12 minutes per each extremity, daily or every other day. Course of treatment is 15-20 procedures.

(l) Spinal Cord Trauma

Treatment is performed after spinal shock and decrease of paresis syndromes, and at the beginning of the regeneration period when the patient's state of health is good. For pain and paraesthesia, a surface electrode is used on forearms and hands, or from the knees to the feet, at medium voltage intensity, beginning with 3 minutes and increasing 1-2 minutes at each subsequent treatment up to a total of 10 minutes per side, daily or every two days. Course of treatment is up to 15 procedures.

(m) Hysterical Disorders of Sensitivity

Treatment is performed by applying a surface electrode on the areas of sensitivity at medium voltage intensity for 5 minutes, daily. Course of treatment is up to 12 procedures.

(n) Hysterical Paralysis

A surface electrode is moved by longitudinal movements from fingers along the whole surface of the arm to the shoulder joint, at high voltage intensity for 10 minutes per each arm, daily. Course of treatment is up to 12 procedures. For astasia abasia treatment is performed in the same manner, from toes to hip joint.

(o) Mutism, Aphonia

An ear electrode is carefully inserted into the external acoustic meatus 1 cm deep, where it is held in position for the whole procedure. Voltage is applied at low intensity for 3-5 minutes per each ear, daily. Course of treatment is up to 12 procedures.

(p) Hearing Loss Due to Meniere's Disease

Between intervals of pain, a surface electrode is moved along the collar zone on the back of neck, and along the upper part of the back to the middle of the shoulder blade, and on at the lower shoulder and and subclavicular areas, at lower voltage intensity for 7-10 minutes, daily or every other day. Course of treatment is up to 10 procedures.

For ear disorders followed by noise in the ears, an ear electrode is inserted into external acoustic meatus 1 cm deep and is held in place. Low intensity voltage is applied for 3-5 minutes. Subsequently a surface electrode is moved by longitudinal or circular movements along the lateral surfaces of the neck at medium voltage intensity for 5 minutes, daily or every other day. Course of treatment is up to 20 procedures.

(q) Migraine, Sleeplessness

A surface electrode is applied to the scalp from the forehead to the back of the head, at low voltage intensity for 5-7 minutes, daily or every other day. Course of treatment is 10-15 procedures. The electrode may also be applied to the collar zone at the back of the neck, moving the electrode along the back surface of the neck and upper part of the back to the middle of the shoulder blade, on the lower shoulder, and on the subclavicular areas of both shoulders, at low voltage intensity, every other day. Course of treatment is 10-15 procedures.

(r) Hiccough

A surface electrode is moved by longitudinal and circular movements along the lateral surfaces of the neck, at medium voltage intensity for 3-5 minutes, daily. Course of treatment is up to 15 procedures.

(s) Neuralgia of Occipital Nerve

For acute and subacute stages, a surface electrode is moved along the back surface of the neck, at medium voltage intensity for 5-10 minutes, daily or every other day. Course of treatment is 12-15 procedures.

(t) Neuralgia of Intra-rib Nerves

For the subacute stage, a surface electrode is moved longitudinally and circularly along the intra-rib spaces, and from the backbone to the chest at medium voltage intensity for 5-10 minutes, daily or every other day. Course of treatment is 10-15 procedures.

(u) Neuralgia Due to Damaged Lateral Femoral Cutaneous Nerve

For treatment of the subacute 'stage (from the eighth day), a surface electrode is moved by circular and longitudinal movements from the inguinal fold to the knee joint, at medium voltage intensity for 5-10 minutes, daily or every other day. Course of treatment is 10-15 procedures.

(v) Neuralgia and Neuritis of Trigeminal Nerve

For acute pain, a surface electrode is moved by circular movements from the scalp to the chin and from the middle of the nose to the floor of the auricle of the injured part of the face, at low voltage intensity for 5-10 minutes, daily or every other day. Course of treatment is 10-15 procedures. The same procedure is used in neuritis of the facial nerve after the acute stage.

(w) Vegetative Polyneuritis

After pain has ceased, a surface electrode is moved by longitudinal movements from the fingers along the whole surface of the arm including the shoulder, lower neck, and thoracic regions of the backbone, at medium voltage intensity for 7-10 minutes for each extremity, every other day. Course of treatment is 10-15 procedures. For severe vascular disorders, the electrode is moved from the toes along the whole surface of the leg including the buttocks and lumbosacral area, at medium voltage intensity for 7-10 minutes per each extremity, every other day. Course of procedure is 10-12 procedures.

(x) Cardiac Pains

For cardiac pain and unpleasant sensations in the heart region caused by a hypersthenic form of neurasthenia, a surface electrode is applied to the heart area and moved by longitudinal and circular movements from the clavicle to the costal arch and from the chest to the left anterior underarm line including the nipple and crown area, at medium voltage intensity for 8-12 minutes, daily or every other day. Course of treatment is 10-15 procedures. To treat unpleasant sensations in the gastroenteric tract, a surface electrode is moved along the anterior abdominal wall from the xiphoid process to the navel and downwards, at medium voltage intensity for 8-12 minutes, daily. Course of treatment is up to 12 procedures.

(y) Retention of Urine

To treat urinary retention caused by myelitis and pelvic disorders, a surface electrode is applied to the lumbosacral areas, perineum and internal surface of upper and lower third region of the thighs, at low or medium voltage intensity for 8-15 minutes, every other day. Course of treatment is 10-15 procedures.

Treatment is contraindicated in myelitis in combination with urosepsis, vast decubitus, and developing myelitis.

(z) Urinary Incontinence

A surface electrode is moved along the perineum and pubis, at low voltage intensity for 5-12 minutes, daily or every other day. Course of treatment is 20 procedures.

(aa) Impotence, Premature Ejaculation

For treatment of premature ejaculation and weak erection due to hypersthenic neurasthenia, a surface electrode is moved by longitudinal and circular movements along the vertebrae at D8-L2, followed by application to the perineum and internal surface of the upper two-thirds of the thighs, at low or medium voltage intensity for 5-15 minutes, daily or every other day. Course of treatment is up to 15 procedures.

For treatment of premature ejaculation and weak erection due to hyposthenic neurasthenia, the same procedure is followed but for a longer period, 15-20 minutes. Course of treatment is up to 20 procedures.

For treatment of atony of the prostate, a straight electrode designed for internal use, such as F1 in FIG. 3, is applied to the prostate gland. The electrode is coated with a lubricant and inserted into the straight intestine 8 cm deep, Voltage is applied at an intensity sufficient for the patient to feel slight heat, for 5 minutes, daily. Course of treatment is up to 15 procedures.

(bb) Parkinson's Disease

Symptoms of Parkinson's disease may be treated by applying a surface electrode to the back, left, and right side of the neck and maxillary and fronal (frontal) sinus at the forehead, at high or medium intensity for 15 minutes, daily. To improve balance, a surface electrode is applied to the ear at medium intensity for 5 minutes per ear, daily. Course of treatment is 10-20 days.

The corona system should not be applied if there is damage in the musculature of the patient's brain vasculature.

(cc) Alzheimer's Disease

Symptoms of Alzheimer's disease may be treated by applying a surface electrode to the back, left and right side of the neck, and maxillary and frontal sinus at forehead, at high and medium intensity. Therapy is applied for 15 minutes, daily. A surface electrode is moved along the scalp at medium intensity for 5 minutes, daily. Course of treatment is 10-20 days. If needed a surface electrode is applied to the ears to improve balance. It is applied at medium intensity, for 5 minutes, for each ear, daily. Course of treatment is 5 days.

The corona system should not be applied if there is damage in the musculature of the patient's brain vasculature.

(6) Orthopaedic Treatment

The corona system may be used to treat sports injuries, such as tennis (lateral epicondylitis) or golfer's (medial epicondylitis) elbow; swimmer's shoulder (rotator cuff tendonitis); patellofemoral pain syndrome; chondromalacia of the patella; infrapatellar tendonitis; anterior cruciate ligament injury, shin splints (medial tibial stress syndrome); Achilles tendon tears; tendonitis; calcification of the neck and joints; and rheumatic diseases. A surface electrode, such as S2 or F2 in FIG. 3, is applied to the affected area at medium voltage intensity for 20 minutes daily. Course of treatment is 5-10 days.

(7) Treatment of Diseases of Internal Organs (a) Chronic Subacid Gastritis

Longitudinal and circular movements of a surface electrode at low to medium voltage intensity are applied to the skin of the epigastric area. Voltage may also be applied to the vertebrae at D7-D12, at medium intensity for 7-12 minutes, daily or every other day. Course of treatment is 15-20 procedures.

(b) Dyskinesia of the Stomach

A surface electrode is applied in circular movements from the costal arch to the navel, then along the vertebrae at D7-D12, at medium or high intensity for 5-12 minutes, daily or every other day. Course of treatment is 15-20 procedures.

(c) Dyskinesia of the Intestine

A surface electrode is moved along the skin over the large intestine from the right inguinal fold to the left inguinal fold, at medium or high intensity for 15 minutes, daily or every other day. Course of treatment 15-20 procedures.

(d) Esophageal Spasms

A surface electrode is applied in longitudinal movements from the upper edge of the chest to the xiphoid process, at medium or high intensity for 5 minutes, daily. Course of treatment is up to 15 procedures.

(e) Atherosclerotic Cardiosclerosis, Stenocardia, Myocardial Dystrophy

For treatment of atherosclerotic cardiosclerosis with stenocardia of angioneurotic character, stenocardia of angioneurotic character, myocardial dystrophia, and for patients at the initial stage of coronary insufficiency, longitudinal and circular movements of a surface electrode are applied to the area of the heart. The electrode is moved from the clavicle to the costal arch and from the chest to the anterior underarm line at the left, excluding the nipple and crown areas. Voltage is applied at medium intensity for 5-10 minutes, daily or every other day. Course of treatment is 15-20 procedures.

(f) Dynamic (Neurogenic) Disorders of Cardiovascular System

For functional (neurogenic) disorders of the cardiovascular system, accompanied by sensory-pain syndrome (unpleasant feelings in heart area, palpitation in case of normal cardiac rhythm, dull ache in the top of the heart, irritation in left shoulder blade, shoulder or arm), and chronic pains which are not connected with physical tension, longitudinal and circular movements of a surface electrode are applied to the area of the heart. The electrode is moved from the clavicle to the costal arch and from the chest to the anterior underarm line at the left, excluding the nipple and crown areas. Voltage is applied at medium intensity for 10-12 minutes, every other day. Course of treatment is 10-15 procedures.

(g) Climacteric Cardiovascular Neurosis

For climacteric cardiovascular neurosis accompanied by unpleasant feelings or pains in heart area, tachycardia, weakness, etc., longitudinal and circular movements of a surface electrode are applied to the area of the heart. The electrode is moved from the clavicle to the costal arch and from the chest to the anterior underarm line at the left, excluding the nipple and crown areas. Voltage is applied at medium intensity for 5-8 minutes, every other day. Course of treatment is 10-12 procedures.

(h) Neurocirculatory Dystonia of Hypertensive Type

A surface electrode is moved along the scalp at low intensity voltage for 10 minutes, daily or every other day. Course of treatment is 15-20 procedures.

(i) Diabetes Mellitus

The corona system may be used for treating concomitant diseases and complications of diabetes, such as maxillary sinusitis, rhinitis, reduced blood circulation of extremities, furunculosis, skin itch, pyoderma, disorders of the peripheral nervous system, the locomotor system, and the digestive organs, and diseases of women's genital organs. For example, a surface electrode may be applied to the foot of a patient with pain, edema, or loss of sensation. Selection of electrode and time and intensity of treatment will depend on the tissue to be treated and the severity of the disorder. Treatment of various disorders accompanying diabetes are described in various sections of Example 4. The corona system should not be used for serious forms of diabetes mellitus in an uncompensated state or in the case of unstable compensation accompanied by cachexia and acidosis.

(7) Treatment of Ear, Nose, and Throat Disorders (a) Laryngotracheitis, Paralysis and Paresis of Larynx Muscles For treatment in the subacute stage, longitudinal and circular movements of a surface electrode at medium intensity are applied along the anterior surface of the neck, for 5-10 minutes, daily. Course of treatment is up to 10 procedures.

(b) Neuritis of the Acoustic Nerve, Loss of Hearing, Noise in Ears

An ear electrode is carefully inserted 1 cm deep into the acoustic meatus and is held in place. Very low intensity voltage is applied for 3-5 minutes. Subsequently, longitudinal and circular movements of the electrode at medium voltage intensity along the lateral side of the neck are applied for 5 minutes, daily. Course of procedure is up to 20 procedures. Treatment should be repeated after 1.5-2 months. The same procedure is followed to treat hearing loss, noise in ears caused by otosclerosis, atherosclerosis, hypertension disease, disorder of water-salt metabolism, catarrh of the middle ear, etc.

(c) Flu Infection, Colds

A surface electrode is applied to the face, particularly the nose, the maxillary sinuses, and the upper lips. During this treatment, the patient should take a deep breath to get as much ozone as possible through the nose to fight viruses at the nasal cavity. The treatment eases breathing and destroys virus on the face. The electrode is applied on the face for 10 minutes, at low or medium intensity, twice daily throughout the infection period. When the electrode passes near the eyes, the patient should close his eyes.

(d) Sinusitis

A surface electrode is applied to the sinus area of the face for 10 minutes at medium or high intensity, twice daily, throughout the affected period. Low burst mode is preferred.

The treatment disperses the edema at the sinuses. If antibiotics are taken in parallel, the treatment may also improve delivery of the antibiotics to the sinus area.

(8) Dental Treatment

A metallic wire with a plastic holder can be connected at the tip of the electrode (see exemplary electrode S1+EA1 in FIG. 3 and exemplary wire holder in FIG. 9) to create further applications. The modified electrode functions as a micro-coagulator when used for one minute, as a micro-cutter when used for 2 minutes, and as an ozone producer to sterilize a surface when used for 3-5 minutes. An electrode with this modification can be used in dentistry to stop root canal bleeding and to sterilize the root canal.

Although the invention is illustrated and described herein with reference to specific embodiments, the invention is not intended to be limited to the details shown. Rather, various modifications may be made in the details within the scope and range of equivalents of the claims and without departing from the invention. In particular, the recitation in the specification herein of particular voltages, frequencies, periods of treatment, and numbers of treatments are meant to convey the best modes contemplated at this time, but are not necessarily intended to limit the invention in any way.

What is claimed is:

1. A system for treating a medical disorder in a patient in need thereof, the system comprising a source of variable AC voltage having a voltage in a range of about 500-2000 volts, and at least one sealed glass electrode filled with inert gas and connected to the source, the source adapted to energize the electrode at a constant frequency, the glass electrode containing therein a metallic electrode plate connected to a metallic wire for conducting the variable AC voltage to the plate from the source, the glass electrode having an application region configured for placement in contact with an area of skin or mucosa of the patient, the glass electrode configured such that when the application region of the glass electrode is placed in contact with an area of skin or mucosa of the patient and the metallic electrode plate is sufficiently energized by the source, the inert gas inside the glass electrode becomes ionized sufficiently to allow the glass electrode to conduct high frequency current to the area of skin or mucosa, the high frequency current having a frequency in a range of about 10-100 kHz.

2. The system of claim 1, wherein the source is sized to provide voltage to the glass electrode sufficient to reduce the concentration of calcium ions in tissue in the area of the glass electrode such that the reduction in the concentration of calcium ions relaxes blood vessels in the area of the at least one electrode.

3. The system of claim 1, wherein the medical disorder is edema.

4. The system of claim 1, wherein the glass electrode comprises electron tube glass, kovar wire, and a nickel chromium plate.

5. The system of claim 1, wherein the glass electrode comprises a bulbous application region with an outermost surface and a tubular structural region, the application region having a larger diameter than the tubular structural region, and the outermost surface of the bulbous application region is flat, convex, or concave.

6. The system of claim 1 wherein the glass electrode further comprises a structural region, wherein the application region comprises a single layer of glass and the structural region comprises a double layer of glass.

7. The system of claim 6, wherein the application region and the structural region of the glass electrode are tubular, and wherein the application region is shorter than the structural region.

8. The system of claim 6, wherein the application region and the structural region of the glass electrode are tubular, and wherein the application region is longer than the structural region.

9. The system of claim 6, wherein the application region and the structural region of the glass electrode are tubular, and wherein the application region is shorter than the structural region and is positioned at an angle to the structural region.

10. The system of claim 6, wherein the application region of the glass electrode is shorter than the structural region and wherein the application region is spatulate.

11. The system of claim 6, further comprising a metal wire affixed externally to the glass electrode.

12. The system of claim 1, comprising two glass electrodes, wherein one glass electrode is grounded and the other glass electrode connected to the source.

13. The system of claim 1, wherein the inert gas contained within the energized glass electrode is a gas capable of emitting ultraviolet waves when sufficiently energized.

14. A method of treating a medical disorder in a patient in need thereof using the system of claim 1, comprising the steps of placing the glass electrode in contact with the area of skin or mucosa of the patient, energizing the glass electrode sufficient to ionize the inert gas in the electrode, and conducting the high frequency current to the patient.

15. The method of claim 14 comprising (a) applying the electrical voltage to the glass electrode in contact with the area of skin or mucosa of the patient for a period of time sufficient to initiate an improvement in the disorder; and (b) repeating the application of voltage at periodic intervals.

16. The method of claim 15, wherein the frequency of the high frequency current is in a range of 20-50 kHz.

17. The method of claim 16 wherein the frequency of the high frequency current is 25 kHz.

18. The method of claim 15, wherein the voltage is applied continuously.

19. The method of claim 15, wherein the voltage is applied in bursts.

20. The method of claim 15, wherein the medical disorder is selected from the group consisting of edema, burns, lesions, and wounds.

21. The method of claim 15, wherein the medical disorder is a neurological disorder.

22. The method of claim 15, wherein the medical disorder is a skin, hair, or nail disorder.

23. The method of claim 15, wherein the medical disorder is a disorder of genital organs.

24. The method of claim 15, wherein the medical disorder is an orthopedic disorder.

25. The method of claim 15, wherein the medical disorder is a disorder of ear, nose or throat.

26. The method of claim 15, wherein the medical disorder is a disease of an internal organ.

27. The method of claim 15, wherein the medical disorder is a disorder of the circulatory system.

28. The method of claim 15, wherein the medical disorder is a disorder of the intestinal tract.

29. The method of claim 15, wherein tissue regeneration is stimulated.

30. The method of claim 14, further comprising improving delivery of a drug to a specific site proximate to the area of skin or mucosa to which the electrical voltage is applied, comprising the steps of (a) administering a drug to the patient and (b) conducting the high frequency current to the patient via the glass electrode in contact with the area of skin or mucosa for a period of time sufficient to stimulate blood circulation in the specific site, wherein the drug is delivered to the specific site by the stimulated blood circulation.

31. The method of claim 30, wherein the frequency of the high frequency current is in a range of 20-50 kHz.

32. The method of claim 30, wherein the frequency of the high frequency current is 25 kHz.

33. The method of claim 30, wherein the voltage is applied continuously.

34. The method of claim 30, wherein the voltage is applied in bursts.

35. The method of claim 14, comprising sufficiently energizing the glass electrode to cause ultraviolet waves to be emitted by the inert gas contained in the glass electrode.

36. The method of claim 14, comprising sufficiently energizing the glass electrode to cause the inert gas contained in the glass electrode to give off a corona discharge.

37. The method of claim 36, wherein method of treating-the medical disorder further comprises producing ozone from the corona discharge for sterilizing the area of skin or mucosa to which the electrode is applied.

38. The method of claim 14, comprising conducting the high frequency current to the patient for a period of time sufficient to alleviate edema.

* * * * *